United States Patent
Witzel et al.

Patent Number: 5,360,019
Date of Patent: Nov. 1, 1994

[54] ADJUSTABLE LIMB HOLDER APPARATUS

[76] Inventors: Steven M. Witzel, 2754 N. Hampden Ct., Chicago, Ill. 60614; Marshall Witzel, 2733 Hawthorne, Wilmette, Ill. 60091

[21] Appl. No.: 992,844
[22] Filed: Dec. 16, 1992
[51] Int. Cl.⁵ ............................................. A61F 5/37
[52] U.S. Cl. .................................. 128/878; 128/879; 128/DIG. 15
[58] Field of Search ............... 128/875, 876, 877, 878, 128/DIG. 15; 602/20, 21, 62, 63, 64

[56] References Cited

U.S. PATENT DOCUMENTS

| | | | |
|---|---|---|---|
| 2,450,162 | 9/1948 | Promen | 128/878 |
| 2,706,477 | 4/1955 | Daake | 128/878 |
| 2,848,993 | 8/1958 | Terrell | 128/875 |
| 2,998,008 | 8/1961 | Klesa | 128/878 |
| 3,535,719 | 10/1970 | Murcott | 128/876 |
| 3,536,068 | 10/1970 | Stubbs | 128/878 |
| 4,628,925 | 12/1986 | Witzel | 128/133 |
| 4,788,941 | 12/1988 | Villeneuve | 128/876 |
| 4,905,713 | 3/1990 | Morante | 128/875 |
| 5,031,639 | 7/1991 | Wolfer | 128/875 |

Primary Examiner—Michael A. Brown
Attorney, Agent, or Firm—Dick and Harris

[57] ABSTRACT

An adjustable limb holder apparatus for use in securing a patient's limb to a fixed object, to, in turn, substantially restrain movement of the limb. A cuff member, having a top surface and a bottom surface, is positioned about the limb of the patient, and preliminarily secured in position by cooperating cuff retention members operably attached to a portion of the top and bottom surfaces of the cuff member. A strap provides operable secured cooperation between the cuff member and the fixed object, and is attached to a substantially central region of the top surface of the cuff member. Attachment of the strap to the substantially central region serves to preclude the inadvertent, potentially painful and injurious, constriction of the strap about the limb—wherein such constriction would otherwise be caused as the result of the strap inadvertently tightening about the limb during movement of the substantially restrained limb in a direction away from the fixed object.

9 Claims, 2 Drawing Sheets

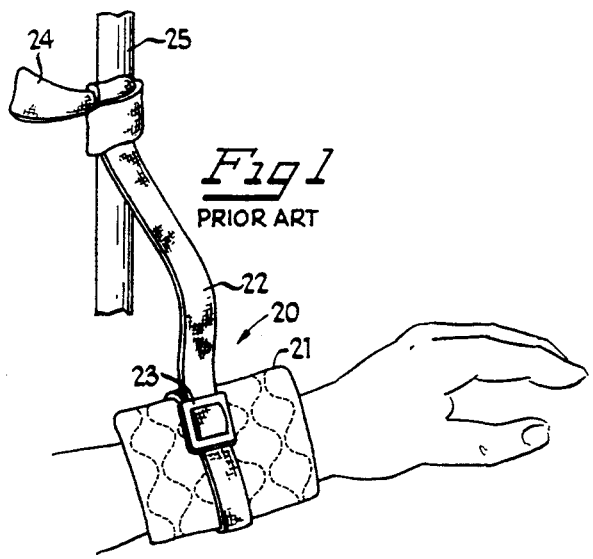
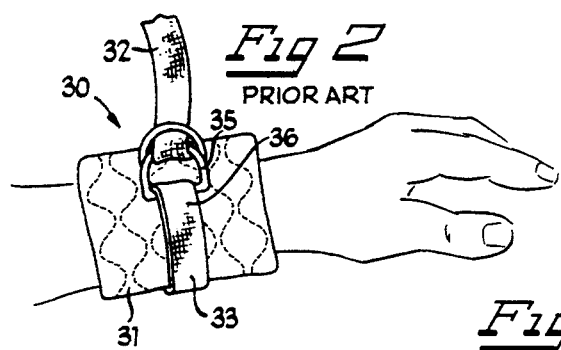
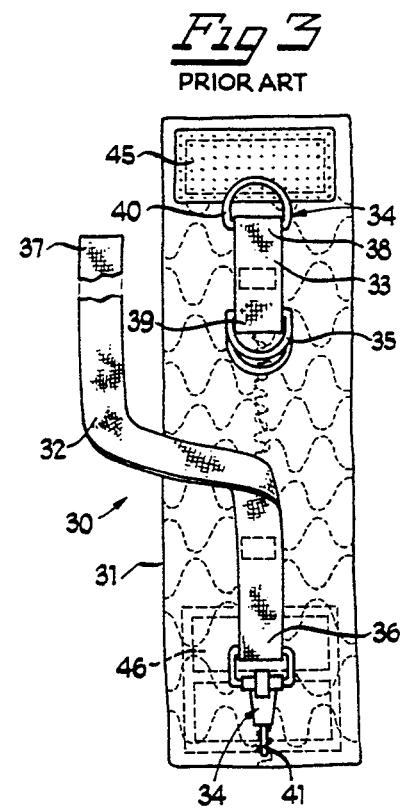
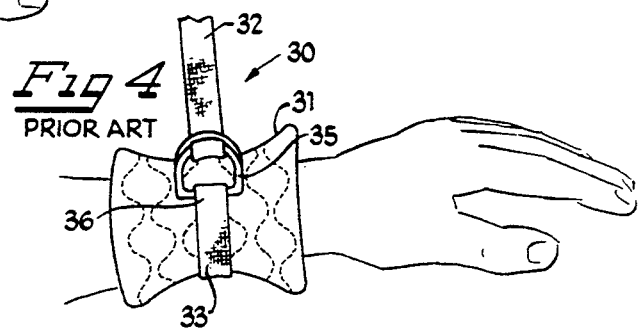
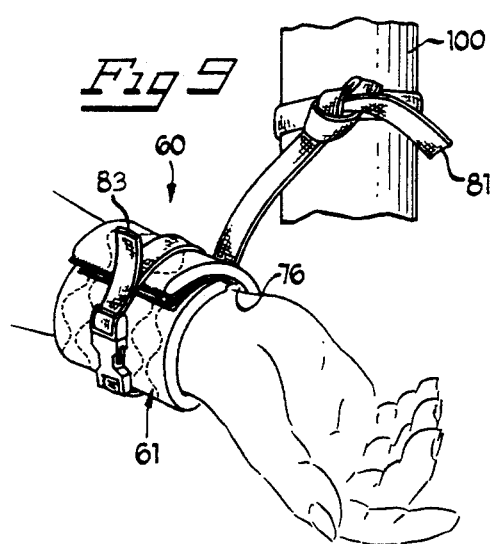
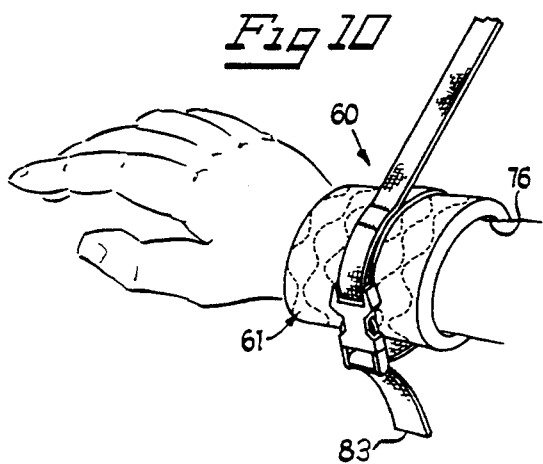

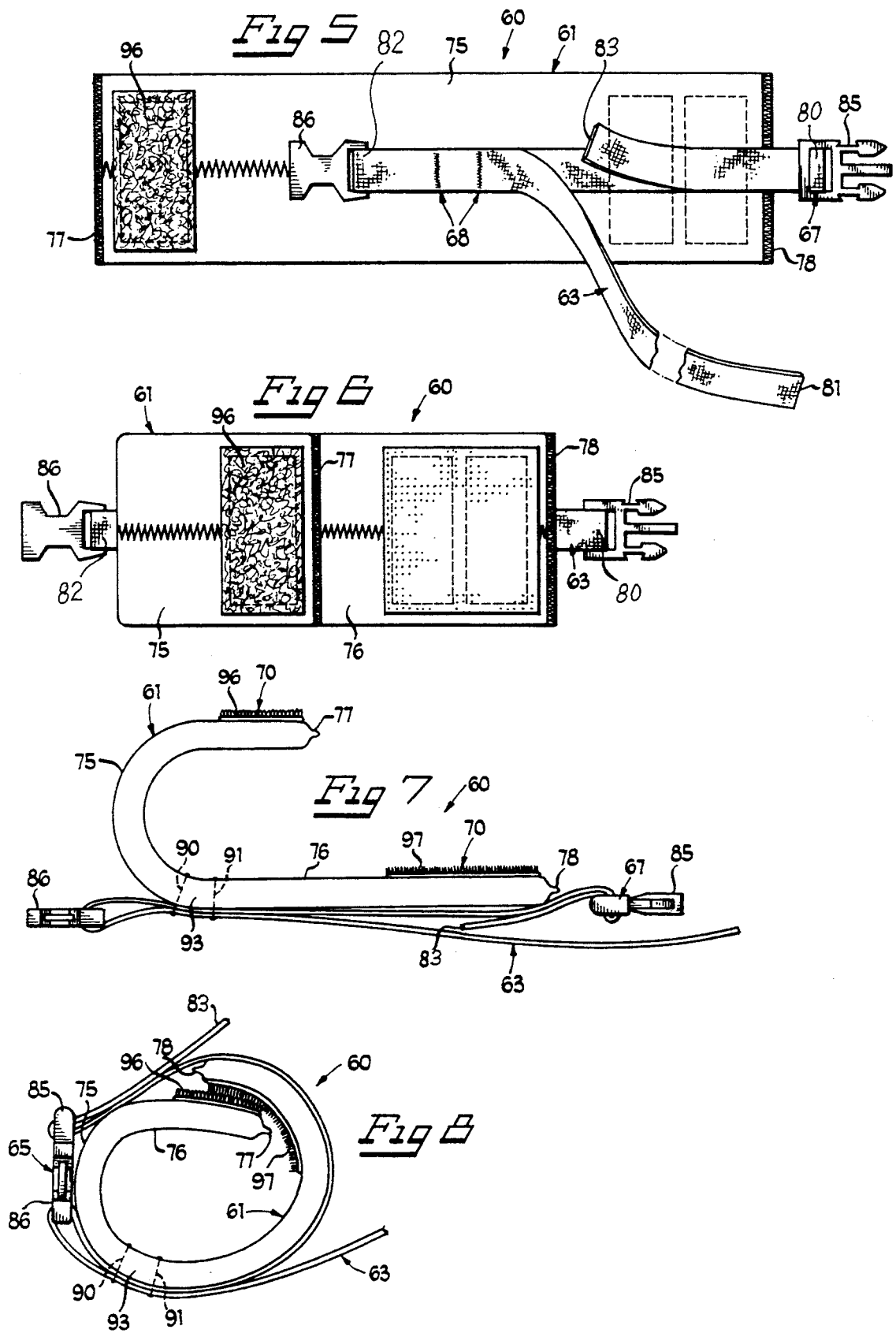

ADJUSTABLE LIMB HOLDER APPARATUS

BACKGROUND OF THE INVENTION

The present invention relates in general to limb restraining devices, and, in particular, to an adjustable limb holder apparatus wherein the apparatus will not inadvertently tighten, or loosen, after appropriate adjustment has been made—so as to preclude inadvertent, potentially painful and injurious, constriction of the apparatus about the restrained limb during movement by the patient.

Limb restraining devices have been utilized for many years to substantially immobilize one or more limbs of a patient by securing such limbs to a relatively fixed object, such as a bed post. Such prior art devices have typically included a cuff member, which can be preliminarily secured about a limb of a patient to be restrained, and one or more straps. The straps, at least one of which may be operably attached to the cuff member, cooperate with an adjustment member so as to facilitate appropriate adjustment of the straps about the cuff member, and, in turn, about the limb of the patient. Such adjustment is intended to ensure that the restraining device is tight enough so as to substantially preclude the restrained limb from slipping out of securement from the cuff member. Substantial immobilization of the limb to be restrained is then achieved by merely securing one end of one of the straps to the fixed object. An example of one prior art limb restraining devices can be found in Witzel, U.S. Pat. No. 4,628,925.

Although many prior art limb restraining devices have been effective in substantially immobilizing the limbs of a patient, problems with use of some of these devices have occurred occasionally when the patient attempts to move the substantially restrained limb in a direction away from the object to which the strap is affixed. Such movement of the limb, which may result in the strap being pulled or tugged, could cause the previously adjusted strap to inadvertently come out of adjustment, and, in turn, tighten about the cuff member. Indeed, when such tightening occurs, the strap encircled about the cuff member can, on some prior art products, cause excessive constriction thereto, and, in turn, to the limb—potentially exposing the patient to unnecessary pain, and, with some devices, injury, to the restrained limb.

Accordingly, it is an object of the present invention to provide an adjustable limb holder apparatus which isolates tension caused to the strap member, as a result of attempted movement of the substantially restrained limb by the patient, between a substantially central region on the cuff member and the object to which the strap is affixed—so as to prevent potential painful and injurious constriction which may otherwise result from the strap encircling the cuff member during such attempted movement of the substantially restrained limb.

It is also an object of the present invention to provide an adjustable limb holder apparatus wherein the strap member encircling the cuff member, after it has been secured about the limb of a patient, will not inadvertently come out of adjustment as a result of attempted movement of the substantially restrained limb by the patient.

It is yet another object of the present invention to provide an adjustable limb holder apparatus which can be preliminarily adjusted so as to conform to different size limbs.

These and other objects of the present invention will become apparent in light of the present specification, claims and drawings.

SUMMARY OF THE INVENTION

The present invention comprises an adjustable limb holder apparatus for use in securing a patient's limb to a fixed object, to, in turn, substantially restrain movement of the limb and the patient, wherein the apparatus will not inadvertently tighten, or loosen, after initial adjustment has been made, so as to preclude inadvertent constriction by the apparatus to the restrained limb during movement by the patient. The apparatus comprises cuff means for encircling at least a portion of the limb to be restrained. The cuff means has a first end, a second end opposite the first end, a top surface and a bottom surface, wherein at least a portion of the bottom surface is in operable contact with the limb during restraint. Strap means are operably attached to the cuff means for providing operable secured cooperation between the cuff means and the fixed object. The strap means have at least one first end and at least one second end, wherein the first end is operably positioned adjacent the cuff means and the second end is operably attachable to the fixed object.

Securement means are provided to operably cooperate with the cuff means for releasably maintaining the cuff means in a restrained orientation about the limb of the patient. The securement means includes coupling means having a first attachment member and a second attachment member releasably attachable to the first attachment member. The first attachment member is operably attached to a portion of the strap means proximate the first end of the strap means, and the second attachment member is operably attached to a portion of the strap means distally spaced from the first end of the strap means, in a position substantially adjacent at least a portion of the top surface of the cuff means and, in turn, distally spaced from the first attachment member. The first and second attachment members, as well as the strap means, are capable of operably encircling a portion of the outer surface of the cuff means after the cuff means has been positioned about the patient's limb for restraint, and after the first and second attachment members have been operably yet releasably attached to each other.

Adjustment means are operably attached to the first attachment member for alternatively tightening and loosening the portion of the strap means operably encircled about the limb of a patient. Constriction preclusion means prevent the adjustment means from inadvertently tightening and loosening after adjustment has been made, and after the second end of the strap means has been attached to a fixed object. Such a construction for maintained adjustment accordingly prevents the strap means from causing otherwise potentially painful and injurious constriction about the restrained limb of the patient as a result of movement by the patient's limb.

In the preferred embodiment of the invention, the constriction preclusion means includes a portion of the strap means adjacent the second attachment member being restrainably secured to the cuff means along a substantially central region of the top surface of the cuff means, so that tension imparted to the strap means, caused as a result of movement of the substantially restrained limb in a direction away from the fixed object, will occur between the substantially central region and the fixed object. Accordingly, the positioning and affixation of a portion of the strap means along the substantially central region of the top surface of the cuff means serves to isolate the strap means between the central region and the first end of the strap means from the tension to, in turn, preclude the adjustment means from inadvertently tightening or loosening about the limb during such movement.

In the preferred embodiment also, the strap means comprises a single strap member operably attached to the cuff means along the top surface of the substantially central region of the cuff means. Furthermore, the first and second attachment members, which may comprise mated, releasable snap-fitting buckles, are each operably attached to the single strap member on opposite sides of the substantially central region.

In this preferred embodiment of the invention, the cuff means is of a length capable of enabling the first end of the cuff means to overlap the second end, while the cuff means completely encircles the limb of the patient to be restrained. The cuff means further includes preliminary cuff retention means operably attached to the cuff means for preliminarily retaining the cuff means in an adjusted overlapped orientation about the patient's limb. The preliminary cuff retention means permit the cuff means to effectively conform to different size limbs, and to further temporarily restrain the patient's limb so as to facilitate attachment of the coupling means, and, the adjustment of the strap means. The preliminary cuff retention means may comprise a first patch of hook and loop fastener elements operably attached to the top surface of the cuff means proximate the first end of the cuff means, and a second mated patch of hook and loop fastener elements operably attached to the bottom surface of the cuff means proximate the second end of the cuff means so as to facilitate releasable and adjustable attachment therebetween. Some of such hook and loop fastener elements are commercially sold under the trademark VELCRO.

BRIEF DESCRIPTION OF THE DRAWINGS

FIG. 1 of the drawings is an elevated side view of a prior art limb holder construction, showing, in particular, a conventional strap, buckle and cuff member, wherein one end of the strap is shown secured to a bed post;

FIG. 2 of the drawings is an elevated side view of another prior art limb holder construction, showing, in particular, a conventional double D-ring adjustment mechanism which accepts the interwinding of a single strap for adjustment thereto;

FIG. 3 of the drawings is a top view of the prior art limb holder construction of FIG. 2, showing, in particular, the quick release attachment mechanism, the preliminary securement patches used to temporarily secure the limb holder apparatus about the limb of a patient, the double D-ring adjustment mechanism attached to one end of the first strap member, as well as showing a second, separate, adjustment strap member having a first end attached to one end of the quick release attachment mechanism and a second end for attachment to a fixed object;

FIG. 4 of the drawings is an elevated side view of the prior art limb holder construction of FIGS. 2 and 3 showing, in particular, the limb holder being potentially tightened about the cuff member, and in turn, about the restrained limb, as a result of tension imparted to the strap about the cuff member, as a result of movement of the restrained limb by the patient.

FIG. 5 of the drawings is a top view of the present adjustable limb holder apparatus, prior to attachment, showing, in particular, the top surface of the cuff means, the single strap means operably attached to the coupling means, the preliminary cuff retention means, the adjustment means, as well as the constriction preclusion means;

FIG. 6 of the drawings is a top view of the present adjustable limb holder apparatus after it has been partially folded over itself, showing, in particular, the first patch of hook and loop fastener elements operably attached to the top surface of the cuff means proximate the first end of the cuff means, and the second patch of hook and loop fastener elements operably attached to the bottom surface of the cuff means proximate the second end of the cuff means;

FIG. 7 of the drawings is an elevated side view of the present adjustable limb holder apparatus, showing, in particular, the positioning of the cuff means after it has been partially folded over itself and toward eventual positioning about the limb of a patient, as well as showing the first and second patches of hook and loop fastener elements and the single attachment of the strap means to the strap attachment position on the top surface of the cuff means;

FIG. 8 of the drawings is an elevated side view of the present adjustable limb holder apparatus, showing, in particular, the preliminary attachment of the cuff means through operable cooperation between the first and second patches of hook and loop fastener elements, the releasable attachment of the first and second attachment members, as well as the single attachment of the strap means to the strap attachment position on the top surface of the cuff means;

FIG. 9 of the drawings is a perspective view of the present adjustable limb holder apparatus after it has been operably attached about the limb of a patient to be restrained, showing, in particular, the positioning of the first end of the strap means attached to the adjustment means, as well as the attachment of the second end of the strap means to a fixed object; and FIG. 10 of the drawings is an elevated perspective view of the present adjustable limb holder apparatus after it has been operably attached about the limb of a patient to be restrained, and after operable adjustment of the strap means has been made, showing, in particular, the constriction preclusion means and the tension imparted to the strap means (caused by movement of the restrained limb) between the strap attachment position on the cuff means and the second end of the strap means when the second end of the strap means is attached to a fixed object (not shown), as well as showing the portion of the strap means between the strap attachment position and the first end of the strap means as being isolated from the tension imparted to the remainder of the strap means.

DETAILED DESCRIPTION OF THE INVENTION

While this invention is susceptible of embodiment in many different forms, there is shown in the drawings and will herein be described in detail, one specific embodiment with the understanding that the present disclosure is to be considered as an exemplification of the principles of the invention and is not intended to limit the invention to the embodiment illustrated.

Prior art limb restraining devices, one of which utilizes a quick release mechanism, are shown in FIGS. 1 through 4. Specifically, prior art limb restraining device 20 is shown in FIG. 1 as comprising cuff member 21, strap member 22 and adjustment buckle 23. Strap member 22 includes a first end (not shown), and a second end 24 which is attached to a fixed object, such as bed post 25. Prior to such attachment, strap member 22 is wrapped around the top surface of the cuff member, and, in turn, about the limb of a patient to be restrained. Once operably positioned, second end 24 of strap member 22 is threaded through adjustment buckle 23, and then pulled until strap member 22 is securely tightened around cuff member 21, and in turn, about the limb of the patient. The second end of the strap member is then secured to bed post 25 (or any other fixed object) so as to substantially restrain the patient's limb from movement.

Prior art limb restraining device 30 is shown in FIGS. 2 through 4 as comprising cuff member 31, first strap member 32, second strap member 33, quick-release member 34 (FIG. 3) and adjustment rings 35. First strap member 32 is shown in FIG. 3 as including first end 36 and second end 37, and second strap member 33 includes distal end 38 and proximal end 39. Quick-release member 34 (FIG. 3) comprises a first D-ring attachment member 40 and a second attachable member 41. First end 36 of first strap member 32 is operably attached to a portion of attachable member 41 of quick-release member 34, and second end 37 of first strap member 32 is operably attachable around a fixed object, such as a bed post (such as shown in FIG. 1). Prior art cuff member 31 additionally includes patches of hook and loop fastener elements, such as VELCRO brand patches 45 and 46 (FIG. 3).

In operation of this prior art device, cuff member 31 is preliminarily secured about the limb of a patient by attaching VELCRO patches 45 and 46 to each other. Once preliminarily secured, second attachable member 41 of quick-release member 34 is operably attached to the D-ring attachment member 40 to further ensure securement about the limb. After such preliminary securement has been maintained, second end 37 of first strap 32 is threaded through the adjustment rings 35, as shown in FIG. 2, and pulled until it is sufficiently tight enough to secure limb restraining device 30 about the limb. Although the prior art, as shown in FIGS. 1 through 4, each securely restrains a limb, problems can occur as a patient strenuously pulls the substantially restrained limb away from the fixed object (such as the bed post, as shown in FIG. 1). When such pulling occurs, the adjusted strap may inadvertently tighten or eventually loosen (after repeated tugs)—wherein such tightening could cause potential excessive constriction about the limb, as shown in FIG. 4, thus potentially causing pain and even minor injury to the limb itself.

Adjustable limb holder apparatus 60 of the present invention is shown in FIGS. 5 through 8 as including cuff means 61, strap means 63, securement means 65 (FIG. 8), adjustment means 67 (FIG. 5 and FIG. 7), constriction preclusion means 68 (FIG. 1) and preliminary cuff retention means 70 (FIG. 7). Cuff means 61 includes top surface 75, bottom surface 76 (FIGS. 6–8), first end 77 and second end 78. As shown in FIGS. 9 and 10, and as will be explained in detail, bottom surface 76 of cuff means 61 will be in physical contact with the limb of a patient to be restrained after adjustable limb holder apparatus 60 has been operably attached about the limb.

Strap means 63 includes a single strap member having a first end 80 (FIG. 5) operably attached to first attachment member 85, second end 81 which is attachable to a fixed object, such as a bed post 100, as shown in FIG. 9, third end 82 operably attached to second attachment member 86, and excess adjustment material end 83. Securement means 65 (FIG. 8), which comprises coupling means, includes first attachment member 85 and second attachment member 86. Although securement means 65 is shown as comprising a releasable biased press fit connector assembly, other types of conventional releasable connectors, such as a buckle, or even the latch-type assembly as shown in FIG. 3, are also contemplated for use.

First attachment member 85 is operably attached to first end 80 of strap means 63, and, second attachment member 86 is operably attached to third end 82 of strap means 63 at a position which is distally spaced from first end 80 of the strap means. Such attachment of the strap means results in second attachment member 86 being positioned substantially adjacent at least a portion of top surface 75 of cuff means 61, prior to attachment about a limb, as well as being distally positioned from first attachment member 85.

Constriction preclusion means 68 (FIG. 5) is shown in FIGS. 7 and 8 as comprising, among other elements, stitched attachment areas 90 and 91. These stitched areas secure a portion of strap means 63, adjacent second attachment member 86, to strap attachment position, at central region 93 of cuff means 61. As will be explained, such attachment of the strap means to the cuff means will serve to isolate the portion of the strap means between central region 93 and first and third ends 80, 82 respectively from tension which may otherwise be imparted thereto as a result of movement of the restrained limb in a direction away from the object to which second end 81 of the strap means is attached. Although stitching is shown for attachment of the strap means to the cuff means, other types of conventional securing techniques and materials are also contemplated for use.

Preliminary cuff retention means 70 is shown in FIG. 7 as including a first patch of hook and loop fastener elements 96 (FIGS. 5–8) operably attached to top surface 75 of cuff means 61, and a second patch of hook and loop fastener elements 97 (FIGS. 7 and 8) operably attached to bottom surface 76 of cuff means 61. The first and second patches of hook and loop fasteners may be releasably attached to each other so as to permit cuff means 61 to effectively conform to the size of the limb to be restrained —prior to secured engagement of first and second attachment members 85 and 86, respectively, about the cuff means, and in turn, about the limb to be restrained. Although hook and loop fastener elements are shown, other types of cooperating fastening devices, such as snaps, buttons and reciprocating straps, among others, are also contemplated for use.

In operation, bottom surface 76 of cuff means 61 is positioned adjacent the limb of a patient which is to be restrained, and it is then wrapped around at least a portion of the limb. In the preferred embodiment, cuff means 61 is of a length capable of enabling its second end 78 to overlap its first end 77 so that cuff means 61 completely encircles the limb of the patient to be restrained (as shown in FIGS. 9 and 10). When such an overlapping occurs, first patch of hook and loop fastener elements 96 and second patch of hook and loop fastener elements 97 will be substantially juxtaposed to each other for operable contact and affixation therebetween. After cuff means 61 has completely encircled the limb, it is overlapped until cuff means 61 operably conforms about the limb where it is then preliminarily secured in place. Such preliminary securement is accomplished by pressing a portion of first patch of hook and loop fastener elements 96, into operable contact with second patch of hook and loop fastener elements 97 as shown in FIG. 8.

As shown in FIGS. 8 through 10, once cuff means 61 is preliminarily secured, first and second attachment members 85 and 86, respectively, of coupling means 65, can be releasably attached to each other. As can be seen, such attachment results in a portion of strap means 63 (in combination with first and second attachment members 85 and 86) completely encircling a portion of top surface 75 of cuff means 61 (FIGS. 9 and 10), and in turn, the limb to be restrained. Appropriate adjustment to adjustable limb holder apparatus 60 is then accomplished by tightening or loosening strap means 63 adjacent adjustment means 67 to a secured, yet non-binding, tightness about the limb. The adjustment means may comprise any conventional adjustment mechanism for use in association with a strap member.

Once strap means 63 completely encircles the cuff means, and, after the first and second attachment members have been coupled to each other, the only physical attachment of the strap means to cuff means 61 will be at substantially central region 93 (FIGS. 7 and 8). Either prior to, or subsequent to operable adjustment of strap means 63, second end 81 of strap means 63 can be secured to a fixed object, such as a bed post 100, as shown in FIG. 9. Although patients having one or more limbs substantially restrained to fixed objects may only occasionally strenuously tug or pull such limbs in a manner which causes tension to the strap means, to in turn, generate constriction of the strap means of prior art devices about the restrained limb or limbs, such inadvertent tightening and constriction of the present invention is substantially reduced or eliminated as a result of constriction preclusion means 68. The constriction preclusion means 68 includes, among other elements, the fixedly restrained joinder of first and third ends 80 and 82 respectively (FIG. 8) of strap means 63 to cuff means 61 through operable attachment at central region 93, between first and second attachment members 85 and 86, respectively; with second end 81 of strap means 63 isolated from interfering with the relative position of said joined first and third ends 80, 82, about cuff means 61, through like affixation at central region 93. Indeed, as previously explained, inasmuch as a portion of strap means 63 adjacent second attachment member 86 is restrainably secured to cuff means 61 at substantially central region 93 of top surface 75 of the cuff means, tension imparted to strap means 63 as the result of movement of the substantially restrained limb in a direction away from the fixed object, such as fixed object 100, as shown in FIG. 9, will be limited to that portion of the strap means between the substantially central region 93 and the fixed object. Inasmuch as the remainder of the strap means, specifically, between the substantially central region 93 and the first end 80 of the strap means, will be isolated from such tension, the strap means will be prevented from substantial, inadvertent tightening or loosening from its adjusted position, and, accordingly, the strap will not cause substantial inadvertent, potentially injurious and painful constriction about the limb during such movement.

The foregoing description and drawings merely explain and illustrate the invention and the invention is not limited thereto except insofar as the appended claims are so limited as those skilled in the art who have the disclosure before them will be able to make modifications and variations therein without departing from the scope of the invention.

What is claimed is:

1. An adjustable limb holder apparatus for use in securing a patient's limb to a fixed object, to, in turn, substantially restrain movement of the limb and, in turn, the patient, wherein the apparatus will not inadvertently tighten, or loosen, after initial adjustment has been made, so as to preclude inadvertent constriction by the apparatus to the restrained limb during movement by the patient, said adjustable limb holder apparatus comprising:

cuff means for encircling at least a portion of the limb to be restrained, said cuff means having a first end, a second end opposite said first end, a top surface and a bottom surface, wherein at least a portion of said bottom surface is in operable contact with the limb during restraint;

strap means operably attached to said cuff means at a strap attachment position for providing operable secured cooperation, without constriction, between said cuff means and said fixed object, said strap means having at least one first end, at least one second end and at least one third end, wherein said first end and said third end operably emanate and are operably distanced from said strap attachment position towards positioning and joinder of said first and third ends, and in turn said strap means about said encircling cuff means, said second end operably emanating and being operably distanced from said strap attachment position and being operably attachable to said fixed object means for precluding operable encircling of a portion of said strap means about said cuff means between said strap attachment position and said second end, where said second end extends from said fixed object directly to said strap attachment position without encircling said cuff means to, in turn, preclude constriction of said portion of said strap means about said restrained portion of said limb, securement means operably cooperating with said cuff means and said first and third ends of said strap means for releaseably maintaining at least a portion of said strap means and said encircling cuff means in a restrained orientation about the limb of the patient, said securement means including coupling means having a first attachment member and a second attachment member releaseably attachable to each other for joining said first and third ends of said strap means into said position about said encircling cuff means in a fixedly restrained manner; substantially resistant to said tension which may be imparted to said strap means by forces applied to said second end and, in turn, said strap attachment position which absorbs forces, to, in turn, isolate said second end from interfering with the relative position of said joined first and third ends of said strap means about said cuff means, said first attachment member being operably attached to a portion of said strap means proximate said first end of said strap means, and said second attachment member being operably attached to a portion of said strap means proximate said third end of said strap means, said first and second attachment members and said operably attached strap means being capable of operably encircling said outer surface of said cuff means after said cuff means has been operably positioned about said patient's limb for restraint and after said first and second attachment members have been operably yet releasably attached to each other, said isolation of said second end from interfering with the relative positions of said joined first and third ends of said strap means about said cuff means to, in turn, substantially preclude said forces applied to said second end from inadvertently tightening the portion of said strap means operably encircling said limb of a patient, and, it turn, preventing said strap means from causing potentially painful and injurious construction about said cuff means and, in turn said restrained limb of the patient during movement of said patient's limb and applications of forces from said second end.

2. The invention according to claim 1 in which said third end of said strap means adjacent said second attachment member is restrainably secured to said cuff means at said strap attachment position along a substantially central region of the top surface of said cuff means so that tension imparted to said strap means at least in part from said second end, caused as a result of movement of the substantially restrained limb in a direction away from the fixed object, will be isolated to occur between said substantially central region and said fixed object at said second end.

3. The invention according to claim 2 in which said strap means comprises a single strap member operably attached to said cuff means along said top surface of said substantially central region of said cuff means.

said first and second attachment members each being operably attached to said single strap member on opposite sides of said substantially central region at said first and third strap ends respectively.

4. The invention according to claim 1 in which said first and second attachment members of said coupling means comprises mated, releasable snap-fitting buckle members.

5. The invention according to claim 1 in which said cuff means is of a length capable of enabling said first end of said cuff means to overlap said second end, while said cuff means completely encircles the limb of the patient to be restrained.

6. The invention according to claim 5 in which said cuff means further includes preliminary cuff retention means operably attached to said cuff means for preliminarily retaining said cuff means in an adjusted overlapped orientation about said patient's limb, said preliminary cuff retention means permitting said cuff means to effectively conform to different size limbs, and to further temporarily restrain said patient's limb to facilitate the positioning of said strap means about said cuff means together towards the attachment of said first and second attachment members.

7. The invention according to claim 6 in which said preliminary cuff retention means comprises a first patch of hook and loop fastener elements operably attached to said top surface of said cuff means proximate said first end of said cuff means, and a second mated patch of hook and loop fastener elements operably attached to said bottom surface of said cuff means proximate said second end of said cuff means so as to facilitate releasable and adjustable attachment therebetween said first and second patches.

8. The adjustable limb holder apparatus according to claim 1 in which the invention further comprises adjustment means operably attached to said first attachment member of said coupling means for alternatively lengthening and shortening a portion of said strap means at said first end for operably and comfortably encircling said cuff means and, in turn, said limb of a patient.

9. The adjustable limb holder apparatus according to claim 8 in which the invention further comprises constriction preclusion means for further preventing said adjustment means from inadvertently tightening and loosening after said strap means has been adjusted, with said first and second attachment members releasably attached to encircle said strap means about said cuff means and, in turn, said patient's limb, after said second end of said forces from said second end of said strap means has been attached to said fixed object, to, in turn, prevent said strap means from causing potentially painful and injurious constriction about the restrained limb of the patient.

* * * * *

UNITED STATES PATENT AND TRADEMARK OFFICE
CERTIFICATE OF CORRECTION

PATENT NO. : 5,360,019
DATED : November 1, 1994
INVENTOR(S) : Steven M. Witzel and Marshall Witzel It is certified that error appears in the above-indentified patent and that said Letters Patent is hereby corrected as shown below:

Column 8, line 67, after relative delete "position" and insert instead --positions --.

Column 9, line 24, Delete the word "construction and insert instead --constriction --.

Signed and Sealed this

Sixth Day of June, 1995

Attest:

BRUCE LEHMAN

Attesting Officer          Commissioner of Patents and Trademarks